(12) United States Patent
Schulz et al.

(10) Patent No.: US 11,433,401 B2
(45) Date of Patent: *Sep. 6, 2022

(54) PURIFICATION SYSTEMS AND METHODS (71) Applicant: AMGEN INC., Thousand Oaks, CA (US)

(72) Inventors: Craig Michael Schulz, Thousand Oaks, CA (US); Justin James Provchy, Simi Valley, CA (US); John Kasajja Kawooya, Moorpark, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/091,481

(22) Filed: Nov. 6, 2020

(65) Prior Publication Data

US 2021/0053073 A1 Feb. 25, 2021

Related U.S. Application Data (62) Division of application No. 16/323,885, filed as application No. PCT/US2017/057788 on Oct. 23, 2017, now Pat. No. 10,940,485.

(Continued)

(51) Int. Cl.
B03C 1/01 (2006.01)
B03C 1/12 (2006.01)
(Continued)

(52) U.S. Cl.
CPC ............... B03C 1/01 (2013.01); B03C 1/10 (2013.01); B03C 1/12 (2013.01); G01N 33/54326 (2013.01)

(58) Field of Classification Search
CPC .................... B03C 1/01; B03C 1/12
See application file for complete search history.

(56) References Cited

U.S. PATENT DOCUMENTS 5,681,478 A 10/1997 Lea et al.
6,764,859 B1 7/2004 Kreuwel et al.
(Continued)

FOREIGN PATENT DOCUMENTS

CN 104094123 A 10/2014
JP H05502294 A 4/1993
(Continued)

OTHER PUBLICATIONS

Singapore Patent Application No. 112019012335, Written Opinion, dated Sep. 2, 2021.
(Continued)

Primary Examiner — Bradley R Spies
(74) Attorney, Agent, or Firm — Marshall, Gerstein & Borun LLP (57) ABSTRACT A purification system and method may include a container receiving portion, pump, and magnetic field generating element. The container receiving portion may be configured to receive and support a container containing a mixture. Magnetic beads may be added to the container for separating a target substance from a remainder of the mixture. The magnetic field generating element may be movable relative to the container receiving portion between a non-working position remote from the container receiving portion and a working position adjacent an outer periphery of the container receiving portion. In the working position, the magnetic field generating element may attract the magnetic beads and hold them firmly against an interior surface of the container. While the magnetic beads are immobilized by the magnetic field generating element, the pump may remove the mixture from the container, leaving behind the magnetic beads bound tightly but reversibly to the target substance.

20 Claims, 6 Drawing Sheets

Related U.S. Application Data (60) Provisional application No. 62/415,448, filed on Oct. 31, 2016.

(51) Int. Cl.
  *B03C 1/10* (2006.01)
  *G01N 33/543* (2006.01)

(56) References Cited

U.S. PATENT DOCUMENTS

| | | | |
|---|---|---|---|
| 7,776,221 B2* | 8/2010 | Brassard | ............... B03C 1/286 210/695 |
| 2003/0054360 A1 | 3/2003 | Gold et al. | |
| 2003/0062314 A1 | 4/2003 | Davidson et al. | |
| 2004/0142384 A1 | 7/2004 | Cohen et al. | |
| 2007/0215554 A1 | 9/2007 | Kreuwel et al. | |
| 2010/0261179 A1 | 10/2010 | Betley et al. | |
| 2011/0098623 A1 | 4/2011 | Zhang et al. | |
| 2013/0011880 A1 | 1/2013 | Barbee et al. | |
| 2013/0248453 A1 | 9/2013 | Allier | |
| 2014/0073517 A1* | 3/2014 | Zhou | ............... C12Q 1/6813 506/9 |
| 2015/0368126 A1 | 12/2015 | Predescu et al. | |
| 2017/0292966 A1 | 10/2017 | Yu et al. | |

FOREIGN PATENT DOCUMENTS

| | | |
|---|---|---|
| JP | 2002-001092 A | 1/2002 |
| JP | 2002515319 A | 5/2002 |
| JP | 2008507705 A | 3/2008 |
| JP | 2009-066476 A | 4/2009 |
| JP | 2011-500056 A | 1/2011 |
| JP | 2014-153104 A | 8/2014 |
| WO | WO-0105510 A1 | 1/2001 |
| WO | WO-2009155384 A1 | 12/2009 |
| WO | WO-2012095369 A1 | 7/2012 |
| WO | WO-2015128725 A1 | 9/2015 |
| WO | WO-2016046402 A1 | 3/2016 |

OTHER PUBLICATIONS

Japanese Patent Application No. 2019-515590, Notice of Rejection, dated Aug. 3, 2021.
International Search Report for International Patent Application No. PCT/US2017/057788, dated Mar. 15, 2018.
Written Opinion for International Application No. PCT/US2017/057788, dated Mar. 15, 2018.
Chinese Patent Application No. 2017800621441, First Office Action, dated Jan. 18, 2022.
Japanese Patent Application No. 2019-515590, Examiner's Decision of Rejection, dated Mar. 22, 2022.

* cited by examiner

PURIFICATION SYSTEMS AND METHODS

CROSS-REFERENCE TO RELATED APPLICATION

This is a divisional of U.S. patent application Ser. No. 16/323,885, filed Feb. 7, 2019, which claims the priority benefit of U.S. Provisional Patent Application No. 62/415,448, filed Oct. 31, 2016, the entire contents of each of which are expressly incorporated herein by reference.

FIELD OF DISCLOSURE

The present disclosure generally relates to purification systems and methods and, more particularly, separating a target substance such as a biomolecule from a sample mixture to facilitate analysis or further processing of the target substance.

BACKGROUND

Various diagnostic and medical research activities require the isolation and purification of a substance, such as a protein, contained in a cell culture or other biological mixture. Some conventional purification processes involve precipitating the target substance out of the mixture by altering the solubility of the target substance. Other conventional purification processes require centrifugation, in which particles of different densities are separated by rotating them about a fixed point at high speeds. Chromatography is another conventional technique and requires passing the mixture through a medium in which its constituent components move at different rates.

Conventional purification processes tend to be time-consuming and/or limited to relatively small sample sizes. Centrifugation, for example, is typically carried out in test tubes, each of which may have volume of less than 20 milliliters (mL). If a sample having a large volume requires purification, it usually must be divided into smaller sample sizes in order to be processed according to conventional purification techniques. The step of dividing the original sample into smaller volume samples increases processing time and/or labor. Furthermore, distributing the original sample across multiple containers or wells may enlarge the footprint or workstation space needed for the purification system. Also, conventional purification processes can be labor-intensive if, for example, they require a laboratory technician to manually pipette the sample between various containers.

The present disclosure sets forth purification systems and methods embodying advantageous alternatives to existing purification system and methods, and that may address one or more of the challenges or needs mentioned herein, as well as provide other benefits and advantages.

SUMMARY

One aspect of the present disclosure provides a purification system which may include a container receiving portion, a first pump, and a first magnetic field generating element. The container receiving portion may be configured to receive and support a first container containing a mixture. The first pump may be configured to remove the mixture from the first container after a target substance has been separated from a remainder of the mixture. The first magnetic field generating element may be movable relative to the container receiving portion between a first position remote from the container receiving portion and a second position adjacent an outer periphery of the container receiving portion.

Another aspect of the present disclosure provides a purification method which may include: (a) adding a mixture including a target substance to a container; (b) adding magnetic beads to the container; (c) separating the target substance from a remainder of the mixture with the magnetic beads, wherein the target substance temporarily binds to the magnetic beads; (d) applying a magnetic field to hold the magnetic beads against an interior surface of the container; and (e) removing the mixture from the container while the magnetic field holds the magnetic beads against the interior surface of the container.

An additional aspect of the present disclosure provides a purification system which may include a first container, a second container having a smaller volume than the first container, a first magnetic field generating element, and a second pump. The first container may be configured to initially contain a mixture and the magnetic beads for separating a target substance from a remainder of the mixture. The first magnetic field generating element may be positioned adjacent an exterior surface of the second container. The first pump may be configured to transfer the mixture and magnetic beads from the first container to the second container. The second pump may be configured to remove the mixture from the second container. Additionally, the first magnetic field generating element may magnetically attract the magnetic beads to hold the magnetic beads against an interior surface of the second container while the second pump removes the mixture from the second container.

Yet another aspect of the present disclosure provides a purification method which may include: (a) adding a mixture including a target substance to a first container; (b) adding magnetic beads to the first container; (c) separating the target substance from a remainder of the mixture in the first container with the magnetic beads, wherein the target substance temporarily binds to the magnetic beads; (d) transferring a first volume of the mixture and a first quantity of the magnetic beads from the first container to a second container, wherein a volume of the second container is less than a volume of the first container; (e) applying a magnetic field to hold the first quantity of the magnetic beads against an interior surface of the second container; (f) removing the first volume of the mixture from the second container while the magnetic field holds the first quantity of the magnetic beads against the interior surface of the second container; (g) transferring a second volume of the mixture and a second quantity of the magnetic beads from the first container to the second container; and (h) removing the second volume of the mixture from the second container while the magnetic fields holds the first and second quantities of the magnetic beads against the interior surface of the second container.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the embodiments, except as may be explicitly delineated in the corresponding written description. Also, none of the drawings is necessarily drawn to scale.

DETAILED DESCRIPTION

Figure 1:
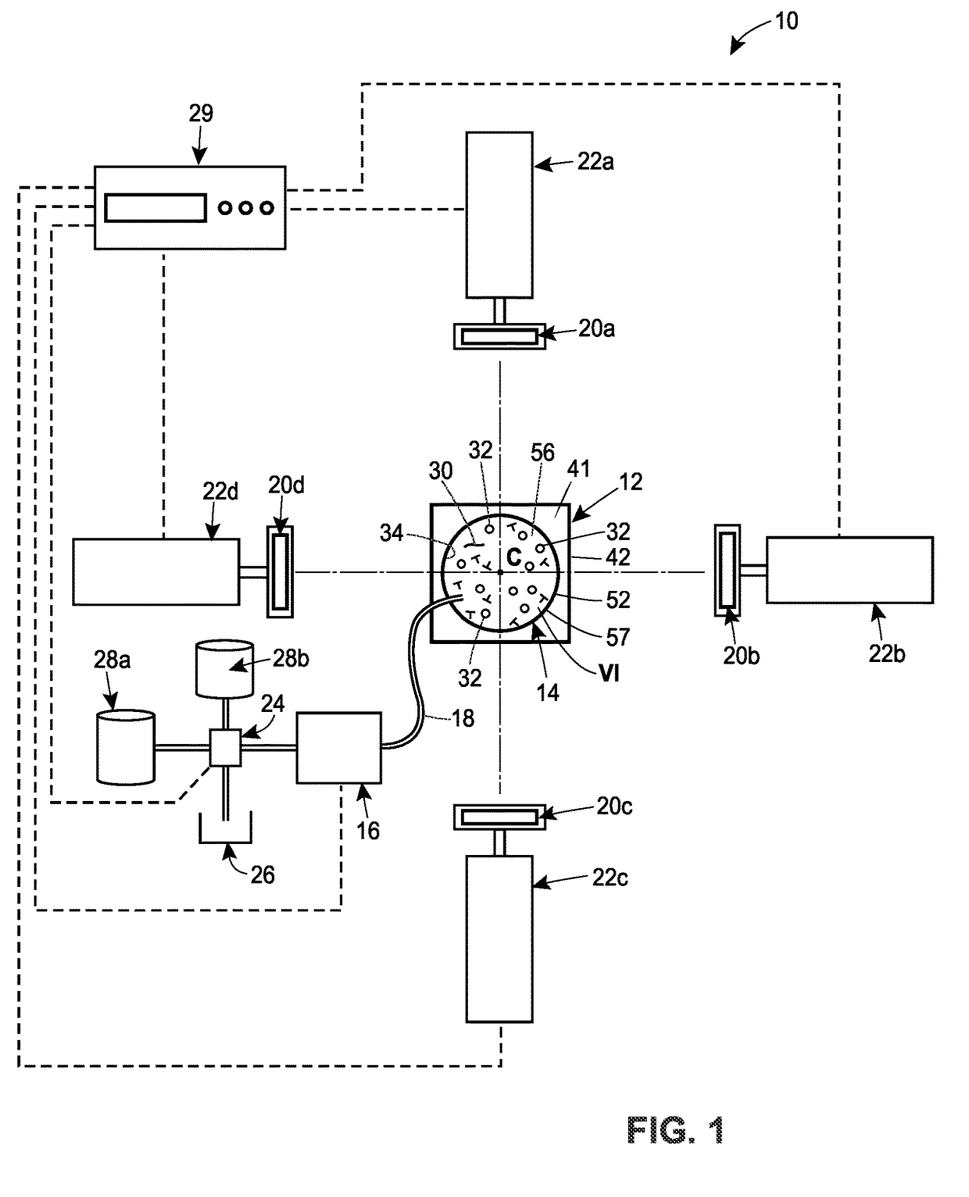
FIG. 1 is a top view of a schematic representation of one embodiment of a purification system constructed in accordance with principles of the present disclosure.

FIG. 1 is a schematic representation of one embodiment of a purification system 10, which can be used to separate a target substance from a mixture, in accordance with principles of the present disclosure. The purification system 10 may include a container receiving portion 12 configured to receive and support a container 14, a pump 16 in fluid communication with the container 14 via a fluid conduit 18, a plurality of magnetic field generating elements 20a-d, and a plurality of actuators 22a-d each configured to move a respective one of the plurality of magnetic field generating elements 20a-d relative to the container receiving portion 12. The container 14 may be filled with a sample mixture 30 including a target substance T. A plurality of magnetic beads 32 may be submerged (e.g., suspended) in the sample mixture 30 for separating or isolating the target substance T from a reminder of the sample mixture 30. Additionally, the pump 16 may be fluidly connected to a multi-position valve 24 such that the pump 16 can selectively discharge waste material to a drain 26 and transfer washing fluids, eluents, and/or other fluids from one or more auxiliary containers 28a and 28b to the container 14. Furthermore, the purification system 10 may include a control unit 29 configured to automatically control operation of the pump 16 and/or the actuators 22a-d.

Generally, during operation of the purification system 10, the container 14 may be placed in the container receiving portion 12, and the actuators 22a-d may reciprocate each of the magnetic field generating elements 20a-d between, depending on the stage of the purification process, a non-working position remote from the container 14 and a working position adjacent (e.g., immediately adjacent but spaced apart, or immediately adjacent and directly contacting) the container 14 and/or the container receiving portion 12. When the magnetic field generating elements 20a-20d are arranged in their respective working positions adjacent the container 14, they may attract the magnetic beads 32 and hold them against an interior surface 34 of the container 14. This may allow the pump 16 to remove the sample mixture 30 from the container 14 while the magnetic beads 32, bound with the target substance T, remain in the container 14 for subsequent washing and/or elution procedures.

So configured, the purification systems and basic methods of the present disclosure advantageously provide an automated or semi-automated process for separating a target substance from a mixture. Furthermore, by virtue of the ability to apply a relatively powerful magnetic field and/or surround the container with multiple magnetic field generating elements, the purification systems of the present disclosure may be able to process sample mixtures with relatively large volumes and quantities of magnetic beads, including samples with volumes equal to or greater than 1 liter (L), for example. Accordingly, the presently disclosed purification systems and methods may eliminate or reduce the need to divide a large volume sample into multiple processing containers, as done in many conventional purification systems and methods. Accordingly, the purification systems and methods of the present disclosure may advantageously provide a faster or more streamlined method of purifying a mixture, and also may reduce the footprint or workstation space needed to accommodate the purification equipment. Additionally, as will be described further below, the purification systems of the present disclosure may be configured for continuous flow applications in which the container and magnetic field generating elements generally function as a trap for removing magnetic beads from a continuous flow of a sample mixture containing magnetic beads. This may enable the processing of very large samples (e.g., samples with volumes exceeding 20000 L) while minimizing the amount of washing fluids and/or eluents needed to extract the target substance bound to the magnetic beads.

Each of the foregoing components of the purification system 10, and related purification methods, will now be described in more detail.

The purification systems and methods of the present disclosure may be used to separate a wide variety of target substances (e.g., molecules, complexes of molecules, biomolecules, complexes of biomolecules, proteins, protein complexes, peptides, nucleic acid ligands, pathogenic microorganisms, cells, etc.) from a wide variety of sample mixtures (e.g., cell cultures, blood, saliva, mucus, perspiration or sweat, urine, stool, soil, food products, etc.). Also, a wide variety of magnetic beads may be used depending on the target substance T to be isolated and/or the character of sample mixture 30. In some embodiments, the magnetic beads 32 may have a spherical shape and possess a paramagnetic core encased in silica and that is coated with a material that binds or conjugates to the target substance T. The binding action between the magnetic beads 32 and the target substance T may be achieved covalently, non-covalently, electrostatically, through hydrogen bonding, through van der Waals forces, and/or through any other suitable molecular binding process. In at least one embodiment, the sample mixture 30 may be a cell culture, the target substance T in the sample mixture 30 may be an antibody, and the magnetic beads 32 are protein A magnetic beads. In another embodiment, the sample mixture 30 may be a cell culture, the target substance T in the sample mixture 30 may be a HIS-tagged protein, and the magnetic beads 32 may be coated with zinc, copper, or cobalt for protein purification.

A non-limiting list of examples of the types of magnetic beads that may be implemented in the presently disclosed purification systems and methods include: affinity type magnetic beads (e.g., Amine magnetic beads, Aldehyde magnetic beads, Carboxy magnetic beads, CDI magnetic beads, DVS magnetic beads, DADPA magnetic beads, Epoxy magnetic beads, Hydrazide magnetic beads, Hydroxy magnetic beads, Iodoacetyl magnetic beads, NHS magnetic beads, Sulfhydry magnetic beads, Tosyl magnetic beads, Thiol magnetic beads, Silica magnetic beads IDA magnetic beads, etc.); reversed-phase type magnetic beads (e.g., C4 magnetic beads, C8 magnetic beads, C18 magnetic beads, Cyanopropyl magnetic beads, Phenyl magnetic beads, diPhenyl magnetic beads, etc.); ion exchange type magnetic beads (e.g., DEAE Magnetic Beads, PSA Magnetic Beads, SAX Magnetic Beads, WCX Magnetic Beads, SCX Magnetic Beads, Hydroxyapatite Magnetic Beads, etc.); antibody purification type magnetic beads (e.g., Protein A Magnetic Beads, Protein G Magnetic Beads, Protein NG Magnetic Beads, Protein L Magnetic Beads, Quick IgG Pure Magnetic Beads, Antigen Peptide Magnetic Beads, Quick IgM Pure Magnetic Beads, Anti-IgG Magnetic Beads, Quick IgA Pure Magnetic Beads, Thiophillic Magnetic Beads, etc.); antibody immobilization type magnetic beads (e.g., Protein A magnetic beads, Protein G magnetic beads, Protein NG magnetic beads, Protein L magnetic beads, Epoxy-activated magnetic beads, Aldehyde-terminated magnetic beads, Hydrazide-terminated magnetic beads, Carboxyl-terminated magnetic beads, lodoacetyl-activated magnetic beads, Thiol-activated magnetic beads, etc.); recombinant protein purification type magnetic beads (e.g., Ni+charged magnetic beads, Co+ charged magnetic beads, Maltose magnetic beads, Calmodulin magnetic beads, etc.); peptide immobilization type magnetic beads (e.g., Epoxy-activated magnetic beads, Aldehyde-terminated magnetic beads, Carboxyl-terminated magnetic beads, Amine-terminated magnetic beads, lodoacetyl-activated magnetic beads, Thiol-activated magnetic beads, etc.); magnetic beads for DNA or RNA purification; magnetic beads for Endotoxin removal; magnetic beads for abundant protein removal; and/or EDTA magnetic beads.

As used herein, the term "magnetic" is defined to encompass any element that is magnetic, paramagnetic, and/or ferromagnetic. Accordingly, the magnetic beads 32 may be magnetic beads, paramagnetic beads, ferromagnetic beads, or any combination thereof.

In some embodiments, the magnetic beads 32 may have a density that is greater than that of the sample mixture 30, such that the magnetic beads 32 sink to the bottom of the container 14 when the magnetic beads 32 are submerged in the sample mixture 30. In other embodiments, the magnetic beads 32 may have a density which is less than or equal to mixture 30 so that the magnetic beads 32 float or partially float in the sample mixture 30.

Referring still to FIG. 1, the container receiving portion 12 may include a platform 41 for receiving and supporting the container 14. In some embodiments, the container receiving portion 12 may be outfitted with an engagement structure 42 (not shown in FIGS. 2 and 3) for inhibiting lateral movement of the container 14 when the container 14 is disposed on the platform 41. In some embodiments, the engagement structure 42 may include one or more vertically upstanding walls arranged around the perimeter of the platform 41 and forming a sleeve that surrounds the container 14. Each of the vertically upstanding walls may possess a height substantially equal to that of the container 14. Alternatively, the engagement structure 42 may be a relatively short, vertically upstanding rim encircling the base of the container 14. The engagement structure 42 may be useful for inhibiting movement of the container 14 when the magnetic beads 32 initially move into contact with the interior surface of the container 14 due to the magnetic attraction of the magnet field generating elements 20a-d. In embodiments where the container receiving portion 12 includes an engagement structure 42, an outer periphery or perimeter of the container receiving portion 12 may be defined by the engagement structure 42. If the engagement structure 42 is omitted, the outer edge of the platform 41 itself may define the outer periphery or perimeter of the container receiving portion 12. Furthermore, in some embodiments, the engagement structure 42 may act as a stop member for preventing further advancement of the magnet field generating elements 20a-d toward the container 14.

Figure 2:
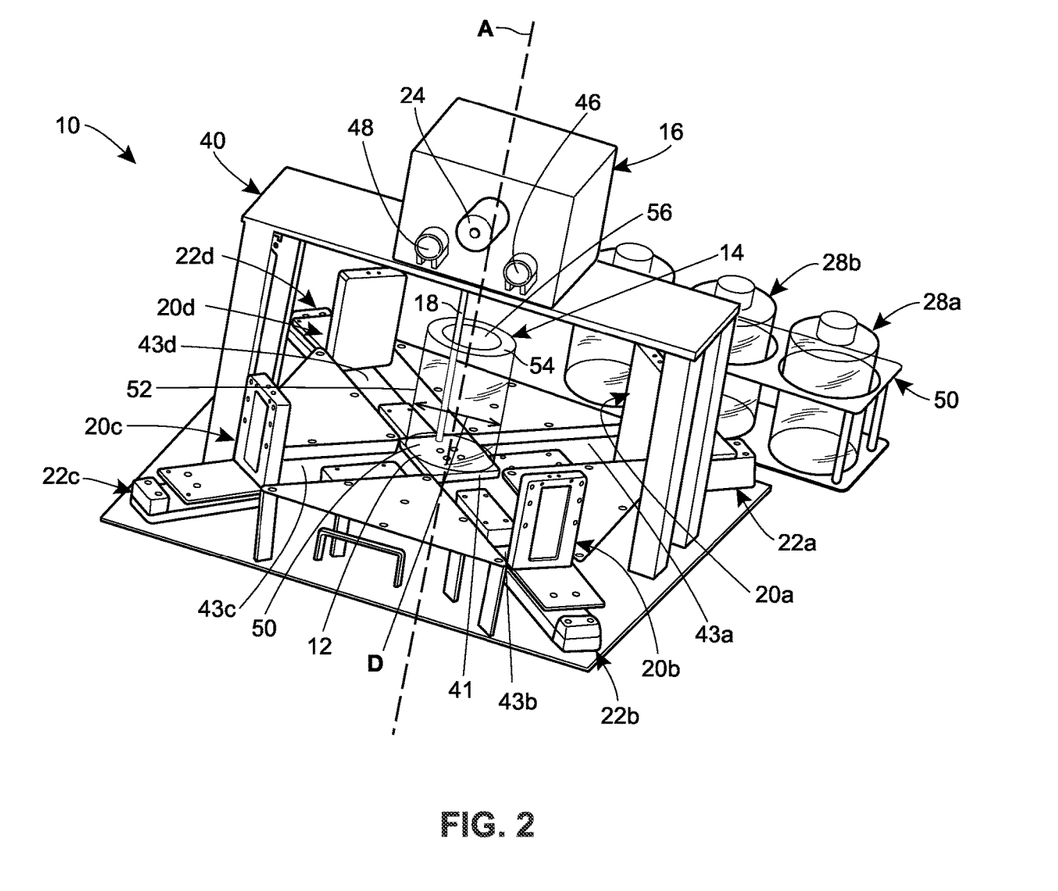
FIG. 2 is a side perspective view of one embodiment of a purification system constructed in accordance with principles of the present disclosure, with the magnetic field generating elements arranged in respective non-working positions.

Turning to FIG. 2, illustrated is a perspective view of one embodiment of the purification system 10, with each of the magnetic field generating elements 20a-d arranged in a non-working position remote from the container 14. The purification system 10 may incorporate a frame 40 or housing to connect and/or support various components including the container receiving portion 12, the pump 16, the magnetic field generating elements 20a-d, and the actuators 22a-d. In the present embodiment, the pump 16 is mounted on top of the frame 40 such that the pump 16 is arranged vertically above the container receiving portion 12. The frame 40 may include channels or slots 43a-d defining fixed horizontal paths for each of the magnetic field generating elements 20a-d. These paths are linear and each is aligned with an imaginary radial line emanating from a center C of the container receiving portion 12. However, in other embodiments, the paths defined by the slots 43a-d may be non-linear, curved, or have any other suitable shape. Furthermore, in some embodiments, the frame 40 may incorporate an enclosure structure (not illustrated) for creating a sealable interior space in which the other components of the purification system 10 can be housed. The enclosure structure may include a door for accessing the interior space, for example, to add and remove the container 14.

Still referring to FIG. 2, the container 14 may include a bottom wall 50 defining a closed end of the container 14, a sidewall 52 extending upwardly from the bottom wall 50 and defining an interior volume V1 of the container 14, and a top wall 54 with an opening 56 defining an open end of the container 14. The sidewall 52 may define the interior surface 34 of the container 14 and an exterior surface 57 of the container 14. A longitudinal axis A of the container 14 may extend between the bottom wall 50 or closed end of the container 14 and the top wall 54 or open end of the container 14. In some embodiments, the top wall 54 may be funnel-shaped so as to form a pouring spout. In the embodiment illustrated in FIG. 1, the top wall 54 may be omitted such that the upper end of the container 14 is defined entirely by the opening 56. A removable cap 58 may cover the opening 56, and may be removed during the purification process so that the fluid conduit 18 (not shown in FIG. 2) can be inserted into the container 14. The container 14 may be made of any suitable material including, for example, glass or plastic. In the embodiment shown in FIG. 2, the container 14 is made of a transparent material. Furthermore, in some embodiments, the container 14 may be a large laboratory beaker.

In the present embodiment, the container 14 has a generally cylindrical shape with a diameter D. The diameter D may be in a range between approximately (e.g., ±10%) 10-60 cm, or approximately (e.g., ±10%) 20-50 cm, or approximately (e.g., ±10%) 35-45 cm, or greater than or equal to approximately (e.g., ±10%) 10 cm, or greater than or equal to approximately (e.g., ±10%) 20 cm, or greater than or equal to approximately (e.g., ±10%) 30 cm. In other embodiments, the container 14 may have a square or rectangular cross-sectional shape, or any other suitable cross-sectional shape. While the container 14 of the present embodiment is configured to hold the mixture 30 in a non-flowing state while the magnetic beads 32 are removed, in alternative embodiments the container 14 may be configured as a conduit (e.g., tubing) through which the mixture 30 and/or other fluids continuously or semi-continuously flow while the magnetic beads 32 are removed and/or trapped.

Generally speaking, the volume V1 of the container 14 may be greater than that of containers or wells used in conventional purification systems. In some embodiments, the volume V1 of the container 14 may be in a range between approximately (e.g., ±10%) 0.5-5.0 L, or approximately (e.g., ±10%) 0.5-4.0 L, or approximately (e.g., ±10%) 0.5-3.0 L, or approximately (e.g., ±10%) 0.5-2.0 L, or approximately (e.g., ±10%) 1.0-3.0 L, or approximately (e.g., ±10%) 1.0-2.0 L, or greater than or equal to approximately (e.g., ±10%) 0.5 L, or greater than or equal to approximately (e.g., ±10%) 1.0 L. As such, a sample mixture with a relatively large volume may be purified without having to divide the sample mixture 30 between multiple processing containers or wells. Instead, the purification process may be carried out in a single container (i.e., the container 14), and, in some cases, the same container that is used to store the sample mixture beforehand can be used in the purification process. As a result of the relatively large volume of the container 14, the purification system 10 may be able to purify a sample mixture up to 10 times faster than conventional purification systems, or even faster.

As illustrated in FIG. 1, the pump 16 may be in fluid communication with the container 14 via the fluid conduit 18. The fluid conduit 18 may be made of flexible tubing, such that the fluid conduit 18 can be bent to side when the container 14 is placed on the container receiving portion 12 and then bent back to its initial position with the distal end of the fluid conduit 18 is inserted into the interior of the container 14. As shown in FIG. 2, the pump 16 may be mounted on the frame 40 such that the pump 16 is located vertically above the container 14. In other embodiments, the pump 16 may be positioned laterally to the side of the container 14 and/or not connected to the frame 40.

In general, the pump 16 is configured to remove and/or add fluids to the container 14 via the fluid conduit 18. The pump 16 may be powered by any suitable means including, but not limited to, an electric motor and/or a source of pressurized hydraulic fluid and/or gas. The pump 16 may be operated at variable speeds or a single speed depending on the specifications of the purification process. In some embodiments, the operation of the pump 16 may be electronically controlled by the control unit 29 according to, for example, programmable instructions stored in a memory of the control unit 29. Alternatively, or additionally, the pump 16 may be operated by an operator (e.g., a laboratory technician) who manually actuates an ON/OFF switch 46 and/or rotates a speed knob 48, as shown in the FIG. 2 embodiment. Furthermore, in some embodiments, the pump 16 may be a positive displacement pump such as a peristaltic pump and capable of pumping a fluid containing suspended solids (e.g., the magnetic beads) without causing damage to them. Such an embodiment of the pump 16 may be utilized by the continuous flow type purification process described below in which the mixture and magnetic beads are transferred together from an incubation container or vat to the container 14. In still further embodiments, the pump 16 may be a centrifugal pump, such as a radial flow pump, which employs a rotating impeller to create a vacuum in order to move fluid. Furthermore, in some embodiments, the pump 16 may be reversible.

Figure 3:
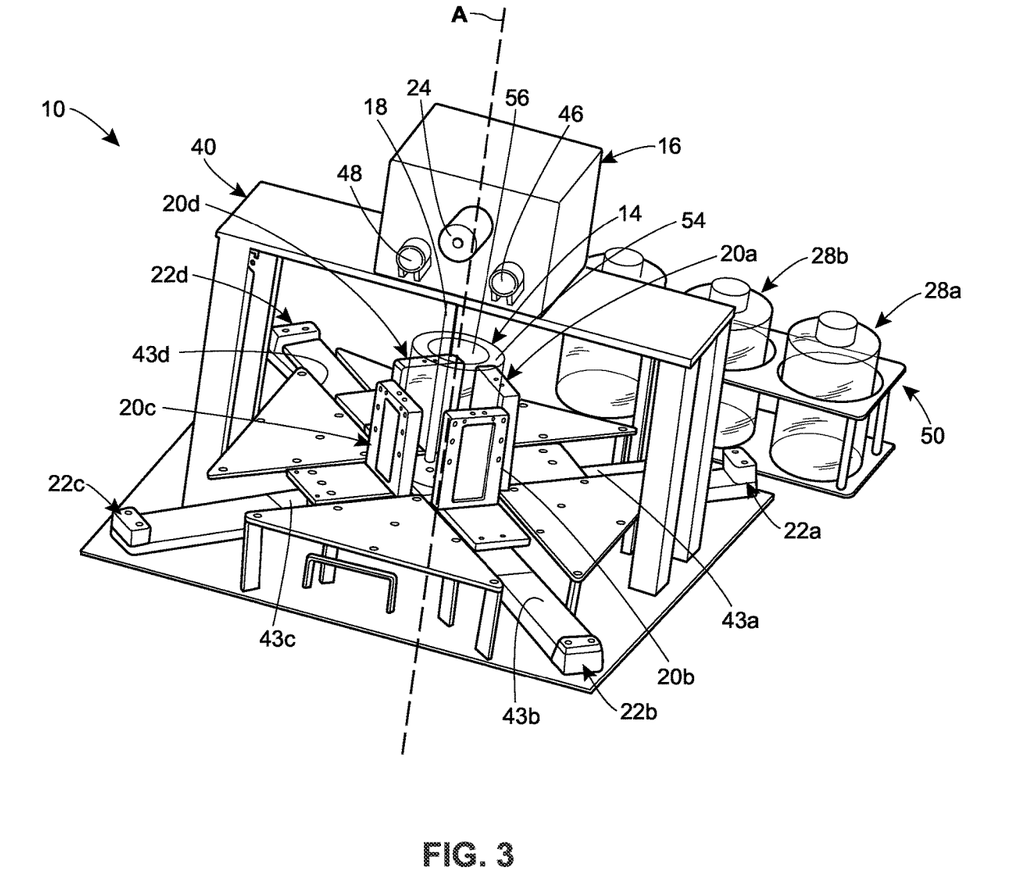
FIG. 3 is a side perspective view of the purification system depicted in FIG. 2, with the magnetic field generating elements arranged in respective working positions.

The multi-position valve 24 may be built into the housing containing the pump 16 as shown in FIGS. 2 and 3, or alternatively, the multi-position valve 24 may be separate from the pump 16 as shown in FIG. 1. The multi-position 24 may enable the pump 16 to be selectively fluidly connected to a variety of different containers (e.g., containers 28a and 28b) and/or the drain 26. In the embodiment shown in FIG. 1, the multi-position valve 24 is a 3-way valve configured to selectively fluidly connect the pump 16 to the drain 26, the container 28a, or the container 28b. In other embodiments, the multi-position valve 24 may be a 2-way valve, or any other valve with any number selectively openable orifices. In some embodiments, the operation of the multi-position valve 24 may be electronically controlled by the control unit 29 according to, for example, programmable instructions stored in a memory of the control unit 29. The multi-position valve 24 may incorporate one or more solenoids for opening and closing orifices of the multi-position valve 24 in response to command signals from the control unit 29. In other embodiments, the multi-position valve 24 may be manually controlled by a user, for example, by rotating a valve knob 48 protruding from the pump housing as shown in FIGS. 2 and 3. In alternative embodiments, a second multi-position valve may be included and configured to selectively fluidly connect the pump 16, or a second pump, to one of several drains or other destinations for the liquid that is aspirated from the container 14.

Referring to FIG. 2, the purification system 10 may include a rack 50 for holding various containers including containers 28a and 28b. In some embodiments, one of the containers held by the rack may serve as the drain 26 illustrated in FIG. 1. The rack 50 may be rigidly connected to the frame 40, or separate from the frame 40. The containers held by the rack 50 may contain washing fluids, eluents, buffers, enzymes, and/or other reagents to be used in the purification process. Also, the rack 50 may be configured hold the sample mixture container 14 prior to the start of the purification process.

FIGS. 2 and 3 shows that the magnetic field generating elements 20a-d are arranged about the outer perimeter of the container receiving portion 12 at equally spaced intervals. In the illustrated embodiment, four magnetic field generating elements 20a-d are included, resulting in 90 degrees of separation between each of the magnetic field generating elements 20a-d. In other embodiments, two, three, five, six, seven, eight, nine, ten, or more magnetic field generating elements may be included. By surrounding the container 14 with multiple magnetic field generating elements, a more uniform magnetic field can be created, which may help ensure that all of the magnetic beads 32 are held and immobilized against the interior surface 34 of the container 14 when the magnetic field generating elements are arranged in their respective working positions (see FIG. 3). In an embodiment where only two magnetic field generating elements are included, each magnetic field generating element may have a C-shaped cross-section, such that moving the two magnetic field generating elements to their respective working positions causes them to encircle the container 14. In still further embodiments, only a single magnetic field generating element may be included, and may generate a magnetic field powerful enough to magnetically attract most or all of the magnetic beads 32 against the interior surface 34 of the container 14, despite being located only on a single side of the container 14.

In some embodiments (such as the one illustrated in the figures), each of the magnetic field generating elements 20a-d is constructed of a respective permanent magnet configured to generate its own persistent magnetic field. Each of the permanent magnets may have a maximum magnetic pull force in range between approximately (e.g., ±10%) 50-1000 Newtons (N), or approximately (e.g., ±10%) 100-800 N, or approximately (e.g., ±10%) 100-700 N, or approximately (e.g., ±10%) 150-600 N, or approximately (e.g., ±10%) 200-500 N, or approximately (e.g., ±10%) 200-450 N, or greater than or equal to approximately (e.g., ±10%) 50 N, or greater than or equal to approximately (e.g., ±10%) 100 N, or greater than or equal to approximately (e.g., ±10%) 150 N, or greater than or equal to approximately (e.g., ±10%) 200 N, or greater than or equal to approximately (e.g., ±10%) 250 N. In some embodiments, the total combined magnetic pull force of the permanents magnets may be greater than or equal to approximately (e.g., ±10%) 500 N, or greater than or equal to approximately (e.g., ±10%) 1000 N, or greater than or equal to approximately (e.g., ±10%) 1500 N, or greater than or equal to approximately (e.g., ±10%) 2000 N, or greater than or equal to approximately (e.g., ±10%) 2500 N. In some embodiments, the permanent magnets constituting the magnetic field generating elements 20a-d may be nickel-plated neodymium block magnets, each having a generally rectangular shape approximately (e.g., ±10%) 5 cm long, 5 cm wide, and 1.25 cm thick. In alternative embodiments, each of the magnetic field generating elements 20a-d may constructed of a respective electromagnet configured to generate a magnetic field when supplied with electric current. In such embodiments, the supply of electricity to the electromagnets may be automatically controlled by the control unit 29.

Each of the magnetic field generating elements 20a-d may be movable, relative to the container receiving portion 12 and/or the container 14, from a respective non-working position remote from the container receiving portion 12 and/or the container 14 (see FIG. 2) to a respective working position adjacent to an outer periphery of the container receiving portion 12 and/or the container 14 (see FIG. 3). The movement between the working and non-working positions may be generally in the horizontal direction and/or a direction that is non-parallel (e.g., perpendicular) to the longitudinal axis A of the container 14. Moving the magnetic field generating elements 20a-d in and out laterally from the sides of the container 14 has the benefit of not obstructing the opening 56 in the top of the container 14, and also eliminates the need to submerge the magnetic field generating elements 20a-d in the sample mixture 30 to attract the magnetic beads 32, which has the risk of introducing contaminants. In the non-working position, the magnetic field of each of the magnetic field generating elements 20a-d may be too weak in the vicinity of the container 14 to effect the position of the magnetic beads 32 in the container 14. In the working position, the magnetic field of magnetic field generating elements 20a-d may be strong enough in the vicinity of the container 14 to magnetically attract the magnetic beads 32 and hold them against the interior surface 34 of the container 14, thereby immobilizing the magnetic beads 32 relative to the container 14. In some embodiments, the distance separating the non-working position and its corresponding working position may fall in a range between approximately (e.g., ±10%) 10-75 cm, or approximately (e.g., ±10%) 20-60 cm, or approximately (e.g., ±10%) 30-45 cm, or greater than or equal to approximately (e.g., ±10%) 20 cm, or greater than or equal to approximately (e.g., ±10%) 30 cm.

As shown in FIGS. 1-3, each of the magnetic field generating elements 20a-d may be configured to move along a respective linear fixed path aligned with a respective imaginary radial line emanating from a center C of the container receiving portion 12 and/or the longitudinal axis A of the container 14 (which may pass through the center C of the container receiving portion 12). In a general sense, the linear fixed paths of the magnetic field generating elements 20a-d may be arranged like spokes on a wheel. Accordingly, the magnetic field generating elements 20a-d each may move inwardly toward to the center C of the container receiving portion 12 when moving from its non-working position to its working position, and each may move outwardly away from the center C of the container receiving portion 12 when moving from its working position to its non-working position. Thus, the distance between the container 14 and each of the magnetic field generating elements 20a-d in its non-working position may be greater than the distance between the container 14 and each of the magnetic field generating elements 20a-d in its working position. In some embodiments, the fixed paths of the of the magnetic field generating elements 20a-d may non-linear, curved, or have any other suitable shape.

Furthermore, each of the magnetic field generating elements 20a-d may have a corresponding actuator 22a-d configured to move the magnet field generating element back-and-forth between the non-working position and the working position. In some embodiments, each of the actuators 22a-d may include a hydraulic or pneumatic cylinder having a reciprocating piston rod. In such embodiments, a single source of pressurized hydraulic fluid or gas (not illustrated) may power each of the hydraulic or pneumatic cylinders. In other embodiments, each of the actuators 22a-d may be powered by a rotating electric motor (not illustrated) via, for example, a pulley system, gear system, or some other motion conversion mechanism. Including actuators 22a-d capable of automatically moving the magnetic field generating elements 20a-d may be beneficial because handling the magnetic field generating elements 20a-d may be dangerous to the health of an operator and/or the memories of personal electronics carried by the operator. Also, if the magnetic attraction between the magnetic beads 32 and the magnetic field generating elements 20a-d is very strong, or if the magnetic attraction among the magnetic field generating elements 20a-d themselves is very strong, it may be difficult and/or cumbersome for an operator to manually move the magnetic field generating elements 20a-d from the working position to the non-working position. Nevertheless, it is possible that in some embodiments, the actuators 22a-d may not be automated, and instead, may be manually powered by a user via, for example, a crank mechanism, or simply by the user pushing and pulling on the actuators 22a-d. In some embodiments, the actuators 22a-d may be configured to move the magnetic field generating elements 20a-d in unison; while in other embodiments, the actuators 22a-d may be configured to move the magnetic field generating elements 20a-d independently of each other.

As shown in FIG. 1, the purification system 10 may include a control unit 29 for controlling the operation of the pump 16, actuators 22a-d, and/or other controllable elements of the purification system 10. The control unit 29 may include a processor (e.g., a microprocessor), a memory (e.g., a random access memory (RAM), a non-volatile memory such as a hard disk executable by the processor, a flash memory, a removable memory, a non-removable memory, etc.) for storing tangible, non-transitory computer-readable instructions, a communication unit, a display, and an input device (e.g., keyboard, keypad, touchscreen, etc.). Furthermore, in some embodiments, the control unit 29 may be a programmable logic controller. The control unit 29 may be programmed to execute a purification process according to an operator's pre-defined specifications. In some embodiments, the control unit 29 may execute steps of the purification process, such as activating the actuators 22a-d to move the magnets 20a-d, in response to sensor data representative of a characteristic of the sample mixture 30 (e.g., the volume, temperature, weight, pH, etc.), a timer, the operator's analog or digital input, and/or any other relevant detectable event or occurrence.

Figure 4A:
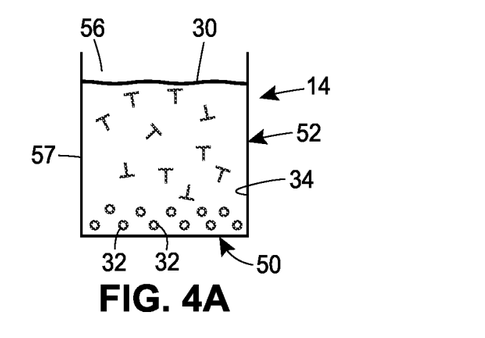
FIGS. 4A-4H schematically illustrate one embodiment of a purification method in accordance with principles of the present disclosure.
Figure 4B:
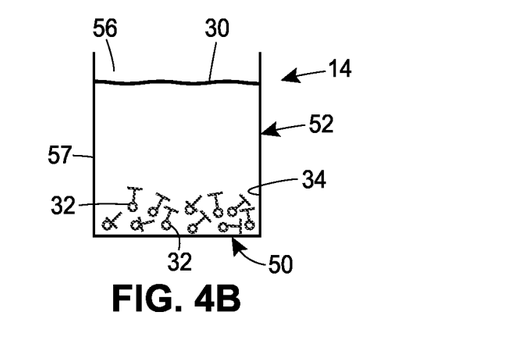

A method of operating the purification system 10 will now be described with reference to FIGS. 4A-4H. For discussion purposes, some of the elements of the purification system 10 are not depicted in FIGS. 4A-4H. Their omission from the figures should not be understood to mean that they are necessarily missing from the purification system 10. As an initial step, the container 14 may be filled with a volume of the sample mixture 30 including the target substance T. Next, as shown in FIG. 4A, the magnetic beads 32 may be added to the container 14 and left to interact with the sample mixture 30 for a period of time (e.g., minutes, an hour, several hours, a day, several days, etc.). During this incubation period, the magnetic beads 32 may bind to the target substance T, thereby separating the target substance T from a remainder of the sample mixture 30 (see FIG. 4B). As mentioned previously, the binding action between the magnetic beads 32 and the target substance T may achieved covalently, non-covalently, electrostatically, through hydrogen bonding, through van der Waals forces, and/or through any other suitable molecular binding process. In some embodiments, the sample mixture 30 may be stirred or agitated during the incubation period to promote binding between the target substance T and the magnetic beads 32. Furthermore, in some embodiments, the container 14 may be placed on the container receiving portion 12 while the magnetic beads 32 bind with the target substance T.

Figure 4C:
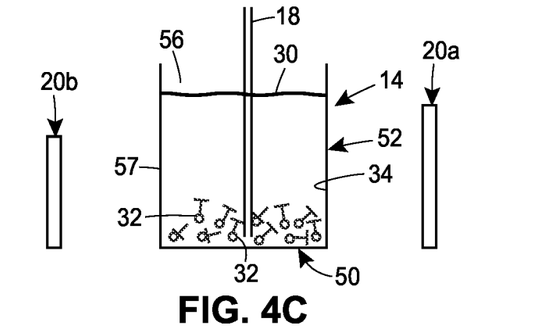

Next, if it has not already been done so, the container 14 may be placed on the container receiving portion 12, with the magnet field generating elements 20a-d each being arranged in their respective non-working positions, as illustrated in FIG. 4C. In some embodiments, the container 14 may be stabilized on the container receiving portion 12 by removable double-sided adhesive sticker pads. The distal end of the fluid conduit 18 may be inserted into the container 14 through the opening 56 and submerged in the sample mixture 30 during this step. The mouth of the fluid conduit 18 may be positioned adjacent or otherwise very close to the bottom wall 50 of the container 14 such that the fluid conduit 18 can aspirate all or substantially all of the sample mixture 30 in the container 14. In an alternative embodiment, the fluid conduit 18 may be fluidly connected to an opening (not shown) in the bottom wall 50 or sidewall 52 of the container 14.

Figure 4D:
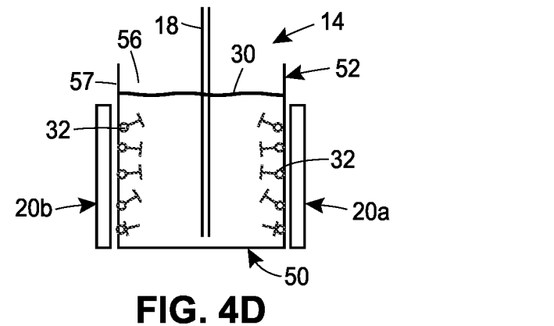

Subsequently, as shown in FIG. 4D, the actuators 22a-d may be activated to move the magnet field generating elements 20a-d inwardly from their respective non-working positions remote from the container 14 to their respective working positions adjacent (e.g., immediately adjacent but spaced apart, or immediately adjacent and directly contacting) sidewall 52 of the container 14 and/or the outer periphery of the container receiving portion 12. FIG. 4D only depicts magnetic field generating elements 20a and 20b, however, all of the magnetic field generating elements 20a-d may be moved from their respective non-working positions to their respective working positions at this stage. As a result, the magnet field generating elements 20a-d may magnetically attract the magnetic beads 32, thereby causing the magnetic beads 32 to be held against the interior surface 34 of the sidewall 52 of the container 14. Friction or contact between the magnetic beads 32 and the magnetized interior surface 34 of the sidewall 52 of the container 14 may effectively immobilize or secure the magnetic beads 32 relative to the container 14, such that the magnetic beads 32 are inhibited or prevented from moving or dispersing during the subsequent removal or addition of fluid to the container 14. In some embodiments, the actuators 22a-d may automatically move the magnet field generating elements 20a-d in response to command signals from the control unit 29. In other embodiments, the actuators 22a-d may powered manually by the operator to move the magnet field generating elements 20a-d.

Figure 4E:
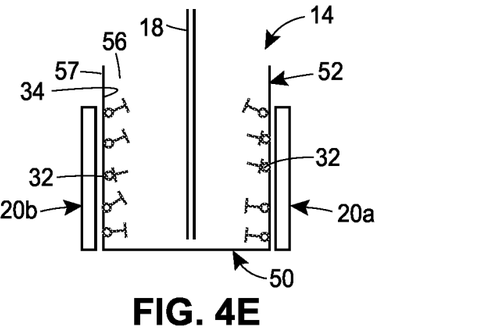

Turning to FIG. 4E, the next step of the purification method may involve aspirating or removing the sample mixture 30 from the container 14 via the fluid conduit 18. In some embodiments, the pump 16 may be used to create the suction needed to remove the sample mixture 30 from the container 14. The magnetic beads 32 are not removed at this step, because they are retained against the interior surface 34 of the sidewall 52 of the container 14 by the magnet field generating elements 20a-20d.

Figure 4F:
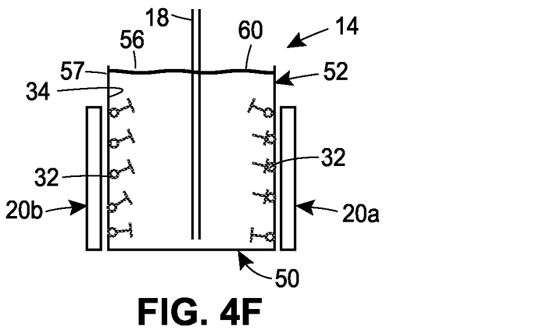

After removal of the sample mixture 30, a washing fluid 60 (e.g., a salt solution) may be added to the container 14 via the fluid conduit 18 or another fluid conduit to clean the interior surface 34 of the container 14 and/or the magnetic beads 32 of any residual mixture, as shown in FIG. 4F. However, the washing fluid 60 may not remove the target substance T from the magnetic beads 32. In some embodiments, the washing fluid 60 may be transferred by the pump 16 from one of the containers (e.g., containers 28a or 28b) held by the rack 50 to the container 14. The volume of the washing fluid 60 added to the container 14 may be equal to or less than (e.g., a fraction of) the maximum volume V1 of the container 14. Optionally, the actuators 22a-d may return the magnets 20a-d to their non-working positions during the washing step, so that the magnetic beads 32 are freely dispersed (e.g., suspended) in the washing fluid 60. Allowing the magnetic beads 32 to disperse may increase the efficacy of the washing process and/or allow stirring, mixing or other agitation of the magnetic beads 32 in the washing fluid 60. Once washing is complete, the actuators 22a-d may move the magnets 20a-d back to their working positions to once again immobilize the magnetic beads 32 against the interior surface 34 of the container 14, and the washing fluid 60 may be removed. Furthermore, in some embodiments, the above-described washing step may be omitted.

Figure 4G:
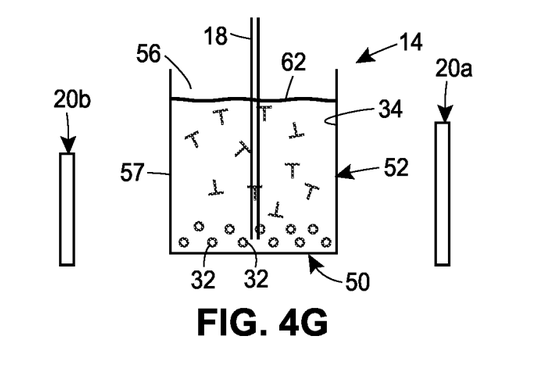

Next, as shown in FIG. 4G, an eluent 62 (e.g., a liquid elution solution) may be added to the container 14 via the fluid conduit 18 or another fluid conduit to cause the target substance T to release from the magnetic beads 32. The actuators 22a-d may be configured to move the magnetic field generating elements 20a-d to their respective non-working positions during the elution step so that the magnetic beads 32 are freely dispersed (e.g., suspended) in the eluent 62; however, moving the magnetic field generating elements 20a-d to their non-working positions at this stage is not required. In some embodiments, the eluent 62 may be transferred by the pump 16 from one of the containers (e.g., containers 28a or 28b) held by the rack 50 to the container 14. In some embodiment, the volume of the eluent 62 transferred by the pump 16 to the container 14 may be equal to or less the volume of the washing fluid 60 previously added to the container 14 during the washing step. Furthermore, in some embodiments, additional steps of adding an enzyme and/or buffer components may be included to, for example, amplify the target substance T in the eluent 62.

Figure 4H:
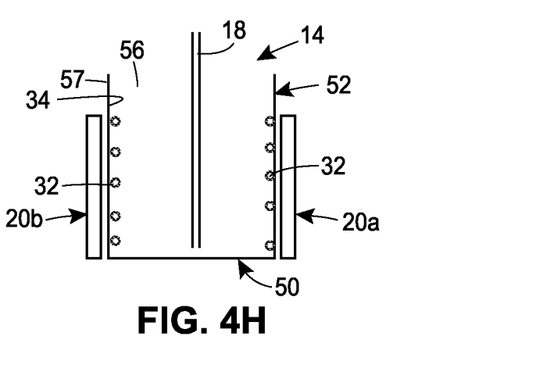

After a period of incubation, the actuators 22a-d may move the magnets 20a-d back to their respective working positions to again immobilize the magnetic beads 32 against the interior surface 34 of the container 14, as shown in FIG. 4H. Then, the pump 14, via the fluid conduit 18, may remove the eluent 62 and the target substance T bound to the eluent 62 from the container 14, and transfer them to one of the containers held by the rack 50 or another container. Finally, the container 14 may be removed from the container receiving portion 12 and discarded or saved for future use. The above-described steps may then be repeated for another container containing another mixture requiring purification.

Although the present embodiment employs the pump 16 to add and remove fluids from the container 14, in alternative embodiments, an operator may manually perform any of the fluid addition or removal steps with, for example, a pipette.

Figure 5:
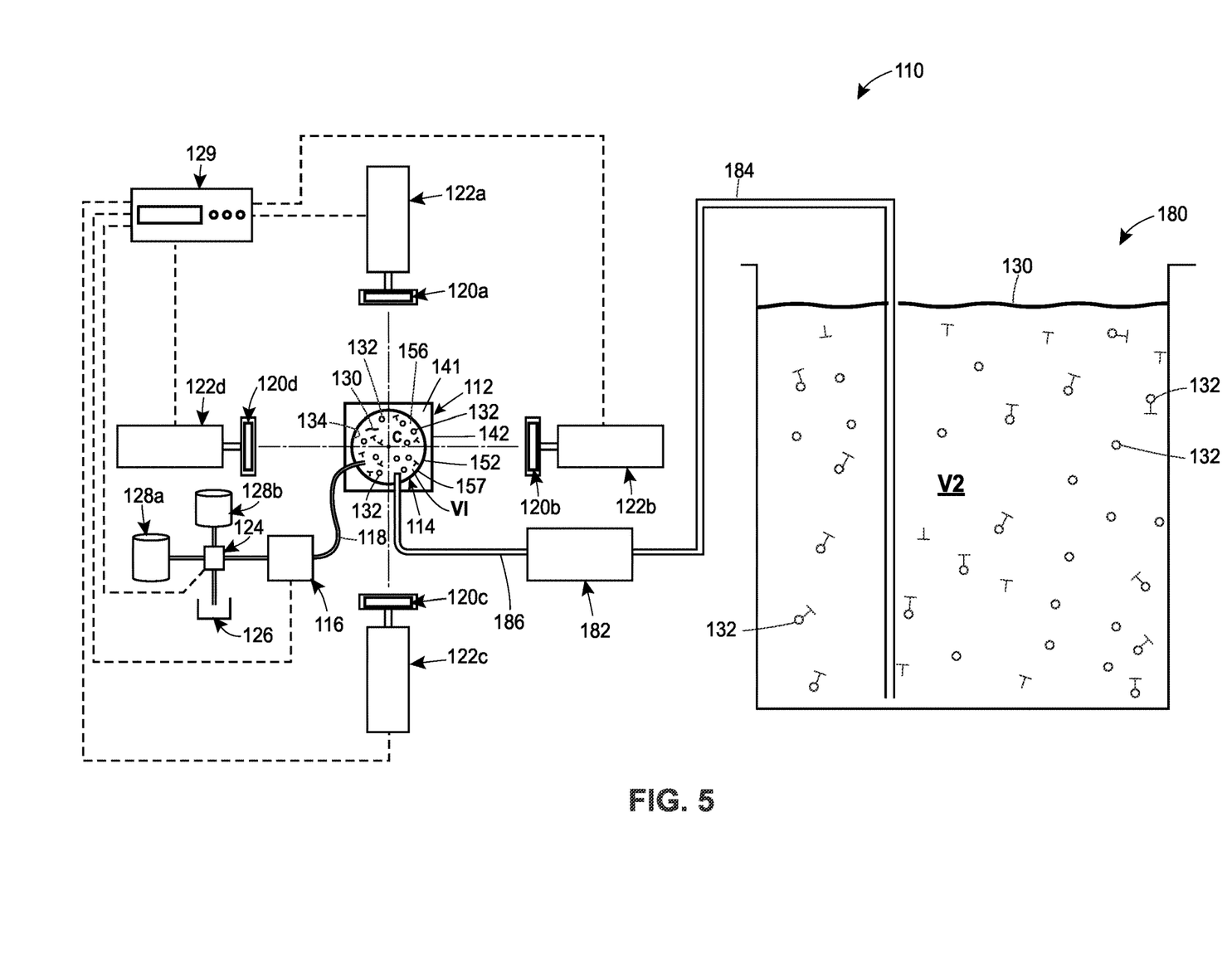
FIG. 5 is a top view of a schematic representation of another embodiment of a purification system constructed in accordance with principles of the present disclosure.

FIG. 5 is a schematic representation of another embodiment of a purification system 110 constructed in accordance with principles of the present disclosure. The purification system 110 is similar in some respects to the purification system 10 described above, except for the addition of an incubation container or vat 180 and a transfer pump 182 to facilitate continuous flow processing of large volume sample mixtures. Elements of the purification system 110 which are the same or similar to the purification system 10 are designated by the same reference numeral, incremented by 100. A description of many of these elements is abbreviated or eliminated in the interest of brevity.

In general, the incubation container 180 may provide a holding space for a large volume sample mixture 130 while magnetic beads 132 submerged in the sample mixture 130 separate a target substance T from a remainder of the sample mixture 130. A volume V2 of the incubation container 180 may be significantly larger than the volume V1 of the container 114. In some embodiments, the volume V2 of the incubation container 180 may be at least 5 times, or at least 10 times, or at least 100 times, greater than the volume V1 of the container 114, or an even higher multiple of the volume V1.

The transfer pump 182 may be configured to transfer the mixture 130 and the magnetic beads 132 from the incubation container 180 to the container 114, which in the present embodiment generally functions as a trap for removing the magnetic beads 132 from the mixture 130. The transfer pump 182 may be fluidly connected to the incubation container 180 via a fluid conduit 184 (e.g., a flexible tube), and fluidly connected to the container 114 via a fluid conduit 186 (e.g., a flexible tube). In some embodiments, the transfer pump 182 may be mounted on the frame 150.

The transfer pump 182 may be configured to remove and/or add fluids to the incubation container 180 via the fluid conduit 184. The transfer pump 182 may be powered by any suitable means including, but not limited to, an electric motor and/or a source of pressurized hydraulic fluid and/or gas. The transfer pump 182 may be operated at variable speeds or a single speed depending on the specifications of the purification process. In some embodiments, the operation of the transfer pump 182 may be electronically controlled by the control unit 29 according to, for example, programmable instructions stored in a memory of the control unit 29. Alternatively, or additionally, the transfer pump 182 may be operated by an operator (e.g., a laboratory technician) who manually actuates an ON/OFF switch and/or rotates a speed knob, for example. Furthermore, in some embodiments, the transfer pump 182 may be a positive displacement pump such as a peristaltic pump and capable of pumping the magnetic beads 132 suspended in the mixture 130 without damaging the magnetic beads 132. In still further embodiments, the transfer pump 182 may be a centrifugal pump, such as a radial flow pump, which employs a rotating impeller to create a vacuum in order to move fluid. Furthermore, in some embodiments, the transfer pump 182 may be reversible.

In the embodiment shown in FIG. 5, the actuators 122a-d are included to move the magnetic field generating elements 120a-d back-and-forth between working positions and non-working positions, similar to the embodiment described above in connection with FIGS. 1-4H. However, in other embodiments, the actuators 122a-d may be omitted, and the magnetic field generating elements 120a-d may be permanently or otherwise fixedly positioned in their respective working position adjacent (e.g., immediately adjacent but spaced apart, or immediately adjacent and directly contacting) the exterior surface 157 of the sidewall 152 of the container 114.

A method of operating the purification system 110 will now be described with reference to FIGS. 6A and 6B. For discussion purposes, some of the elements of the purification system 110 are not depicted in FIGS. 6A and 6B. Their omission from the figures should not be understood to mean that they are necessarily missing from the purification system 110.

Initially, the sample mixture 130 may be added to the incubation container 180, followed by the magnetic beads 132. The magnetic beads 132 may be left to interact with the sample mixture 130 for a period of time (e.g., minutes, an hour, several hours, a day, several days, etc.). During this incubation period, the magnetic beads 132 may bind to the target substance T, thereby separating the target substance T from a remainder of the sample mixture 130.

Figure 6A:
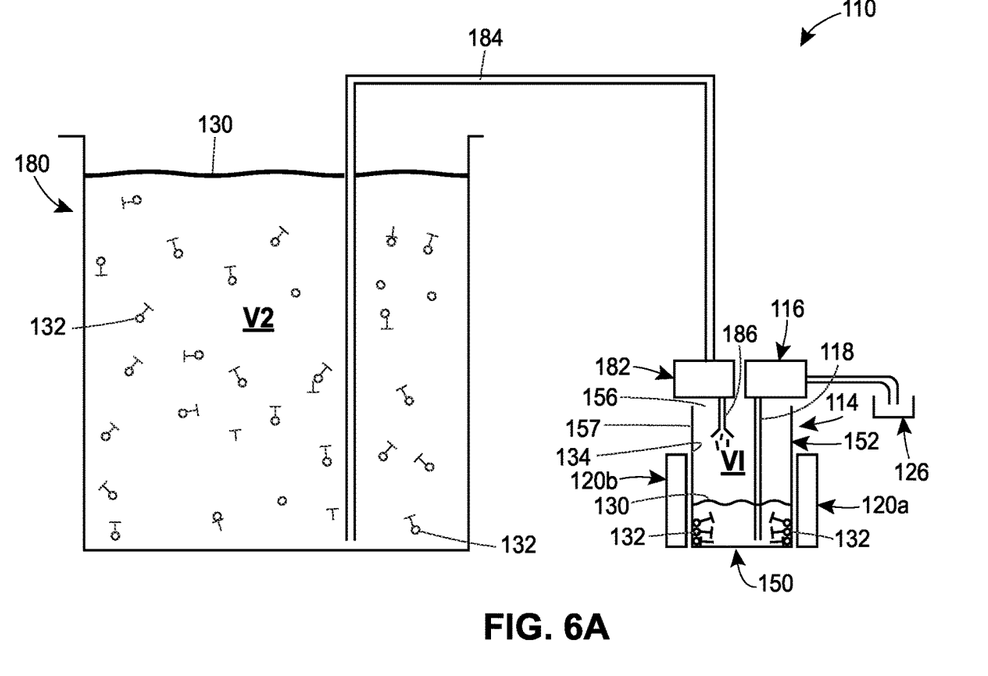
FIGS. 6A and 6B schematically illustrate another embodiment of a purification method in accordance with principles of the present disclosure.
Figure 6B:
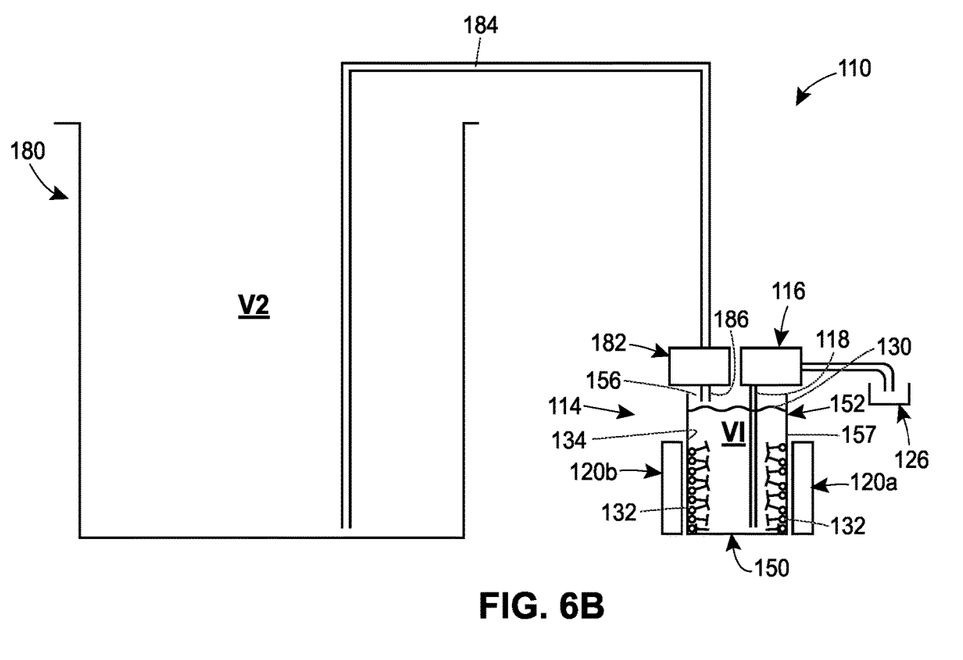

Next, the transfer pump 182 may be activated to begin pumping a first volume of the sample mixture 130 and a first quantity of the magnetic beads 132 suspended in the first volume of the sample mixture 130 from the incubation container 180 to the container 114, as shown in FIG. 6A. Simultaneously, or shortly after the start of the transfer pump 182, the pump 116 may be activated to begin removing the sample mixture 130 from the container 114 and discharging it, for example, to a waste container or the drain 126. Prior to the start of either of the pumps 116 and 182, the magnetic field generating elements 120a-d may be positioned in their respective working positions adjacent (e.g., immediately adjacent but spaced apart, or immediately adjacent and directly contacting) the exterior surface 157 of the sidewall 152 of the container 114. In some embodiments, this positioning of the magnetic field generating elements 120a-d may be accomplished via the actuators 122a-d in a manner similar to that discussed above. In other embodiments, the magnetic field generating elements 120a-d may be permanently or otherwise fixedly positioned in their respective working positions. In either case, the magnet field generating elements 120a-d may magnetically attract the magnetic beads 132 added to the container 114, thereby causing the magnetic beads 132 to be held against the interior surface 134 of the sidewall 152 of the container 114. Friction or contact between the magnetic beads 132 and the interior surface 134 of the sidewall 152 of the container 114 may effectively immobilize or secure the magnetic beads 132 relative to the container 114 when the magnetic field generating elements 120a-d occupy their respective working positions. Accordingly, the magnetic beads 132 are firmly anchored to the wall of the container 114 and thus inhibited or prevented from being removed from the container 114 during the removal of the sample mixture 130 from the container 114 by the pump 116. It is noted that although FIGS. 6A and 6B depict only the magnetic field generating elements 120a and 120b, all of the magnetic field generating elements 120a-d may be positioned in their respective working positions at this stage of the process.

Thereafter, the transfer pump 182 may pump a second volume of the sample mixture 130 and a second quantity of the magnetic beads 132 suspended in the second volume of the sample mixture 130 from the incubation container 180 to the container 114. The pumping of the second volume of the sample mixture 130 and the second quantity of the magnetic beads 132 may begin immediately after the pumping of the first volume of the sample mixture 130 and the first quantity of the magnetic beads 132 such that a uninterrupted, continuous flow of the sample mixture 130 and the magnetic beads 132 from the incubation container 180 to the container 114 is achieved. Furthermore, the pump 116 may be operated to remove the sample mixture 130 from the container 114 simultaneously while the second volume of the sample mixture and the second quantity of the magnetic beads 132 are pumped into the container 114 by the transfer pump 182. Accordingly, an uninterrupted, continuous flow of the sample mixture 130 through the container 114 may be achieved. Throughout this process, the magnetic beads 132 continue to be immobilized against the interior surface 134 of the sidewall 152 of the container 114, as shown in FIG. 6B.

In some embodiments, the transfer pump 182 and the pump 116 may be configured (e.g., controlled by the control unit 129) such that the volumetric flow rate of the sample mixture 130 through the transfer pump 182 is equal to or substantially equal to the volumetric flow rate of the sample mixture 130 through the transfer pump 116. Accordingly, the level of fluid in the container 114 may be kept relatively constant throughout the magnetic bead removal process, except at the very start (when the container 114 is initially filled by the transfer pump 182) and the very end (when the container 114 is drained of all sample mixture 130 by the pump 114).

Once the transfer of material from the incubation container 180 to the trap container 114 is complete, the pump 114 may drain all remaining mixture 130 in the container 114 such that only the magnetic beads 132 bound with the target substance T remain in the container 114. Subsequently, washing and elution steps may be performed in the container 114 similar to those discussed above in connection with FIGS. 4F, 4G, and 4H.

The continuous flow aspect of this purification method makes is suitable for purifying very large sample mixtures, including those with volumes exceeding 20000 L, in an expedient manner. Furthermore, because all of the magnetic beads 132 are washed and/or eluted at the same time in a single container, the amount of washing fluids and/or eluents is reduced as compared to dividing the large volume sample mixture across many processing containers.

While the systems and methods of the present disclosure have been described in connection with various embodiments, it will be understood that the systems and methods of the present disclosure are capable of further modifications. This application is intended to cover any variations, uses, or adaptations of the systems and methods following, in general, the principles of the present disclosure, and including such departures from the present disclosure as, within the known and customary practice within the art to which the invention pertains.

What is claimed is:

1. A purification method comprising:
   adding a mixture including a target substance to a container;
   adding magnetic beads to the container;
   separating the target substance from a remainder of the mixture with the magnetic beads, wherein the target substance temporarily binds to the magnetic beads;
   moving magnetic field generating elements concurrently toward the container to apply a magnetic field to hold the magnetic beads against an interior surface of the container; and
   removing the mixture from the container while the magnetic field holds the magnetic beads against the interior surface of the container.

2. The purification method of claim 1, comprising adding a washing fluid to the container after removing the mixture from the container, and subsequently removing the washing fluid from the container while the magnetic field holds the magnetic beads against the interior surface of the container.

3. The purification method of claim 2, comprising removing the magnetic field after adding the washing fluid to the container so that the magnetic beads are free to disperse in the washing fluid, and subsequently re-applying the magnetic field to hold the magnetic beads against the interior surface of the container during removal of the washing fluid from the container.

4. The purification method of claim 1, comprising adding an eluent to the container after removing the mixture from the container to elute the target substance bound to the magnetic beads, and subsequently removing the eluent and the target substance from the container while the magnetic field holds the magnetic beads against the interior surface of the container, and comprising removing the magnetic field after adding the eluent to the container so that the magnetic beads are free to disperse in the eluent, and subsequently re-applying the magnetic field to hold the magnetic beads against the interior surface of the container during removal of the eluent from the container.

5. The purification method of claim 1, wherein removing the mixture from the container comprises aspirating the mixture from the container via an automated pump.

6. The purification method of claim 1, wherein moving magnetic field generating elements concurrently toward the container to apply a magnetic field to hold the magnetic beads against an interior surface of the container comprises activating an actuator to move at least one magnetic field generating element from a first position remote from the container to a second position adjacent an exterior surface of the container.

7. The purification method of claim 6, wherein the actuator includes a pneumatic or hydraulic cylinder configured to move the at least one magnetic field generating element between the first position and the second position, and wherein the container has an open end and a closed end and a longitudinal axis extending between the open end and the closed end, and wherein the actuator is configured to move the at least one magnetic field generating element in a direction non-parallel to the longitudinal axis when moving the at least one magnetic field generating element from the first position to the second position.

8. The purification method of claim 1, wherein moving magnetic field generating elements concurrently toward the container to apply the magnetic field to hold the magnetic beads against the interior surface of the container comprises arranging a first permanent magnet and a second permanent magnet on opposite sides of the container.

9. The purification method of claim 1, wherein moving magnetic field generating elements concurrently toward the container to apply the magnetic field to hold the magnetic beads against the interior surface of the container comprises arranging a plurality of permanent magnets around a perimeter of the container at equally spaced intervals.

10. The purification method of claim 9, wherein each permanent magnet of the plurality of permanent magnets has a maximum magnetic pull force equal to or greater than 100 N.

11. The purification method of claim 1, wherein the target substance is a biomolecule or the container has a volume equal to or greater than 0.5 L.

12. A purification method comprising:
adding a mixture including a target substance to a first container;
adding magnetic beads to the first container;
separating the target substance from a remainder of the mixture in the first container with the magnetic beads, wherein the target substance temporarily binds to the magnetic beads;
transferring a first volume of the mixture and a first quantity of the magnetic beads from the first container to a second container, wherein a volume of the second container is less than a volume of the first container;
applying a magnetic field to hold the first quantity of the magnetic beads against an interior surface of the second container;
removing the first volume of the mixture from the second container while the magnetic field holds the first quantity of the magnetic beads against the interior surface of the second container;
transferring a second volume of the mixture and a second quantity of the magnetic beads from the first container to the second container; and
removing the second volume of the mixture from the second container while the magnetic field holds the first and second quantities of the magnetic beads against the interior surface of the second container.

13. The purification method of claim 12, wherein removing the first volume of the mixture from the second container comprises removing the first volume of the mixture from the second container while simultaneously transferring the second volume of the mixture and the second quantity of the magnetic beads from the first container to the second container.

14. The purification method of claim 13, comprising
(a) adding a washing fluid to the second container after removing the second volume of the mixture from the second container, and subsequently removing the washing fluid from the second container while the magnetic field holds the first and second quantities of the magnetic beads against the interior surface of the second container, or
(b) removing the magnetic field after adding the washing fluid to the second container so that the first and second quantities of magnetic beads are free to disperse in the washing fluid, and subsequently re-applying the magnetic field to hold the first and second quantities of magnetic beads against the interior surface of the second container during removal of the washing fluid from the second container.

15. The purification method of claim 12, comprising
(a) adding an eluent to the second container after removing the second volume of the mixture from the second container to elute the target substance bound to the first and second quantities of magnetic beads, and subsequently removing the eluent and the target substance from the second container while the magnetic field holds the first and second quantities of magnetic beads against the interior surface of the second container, or
(b) removing the magnetic field after adding the eluent to the second container so that the first and second quantities of the magnetic beads are free to disperse in the eluent, and subsequently re-applying the magnetic field to hold the first and second quantities of the magnetic beads against the interior surface of the second container during removal of the eluent and the target substance from the second container.

16. The purification method of claim 12, wherein transferring the first volume of the mixture and the first quantity of the magnetic beads from the first container to the second container comprises pumping the first volume of the mixture and the first quantity of the magnetic beads via an automated pump, and optionally, wherein removing the combined first and second volumes of the mixture from the second container comprises pumping the combined first and second volumes of the mixture from the second container via the automated pump.

17. The purification method of claim 12, wherein applying the magnetic field to hold the first quantity of the magnetic beads against the interior surface of the second container comprises activating an actuator to move at least one magnetic field generating element from a first position remote from the second container to a second position adjacent an exterior surface of the second container.

18. The purification method of claim 17, wherein
(a) the actuator includes a pneumatic or hydraulic cylinder configured to move the at least one magnetic field generating element between the first position and the second position, or
(b) the second container has an open end and a closed end and a longitudinal axis extending between the open end and the closed end, and wherein the actuator is configured to move the at least one magnetic field generating element in a direction non-parallel to the longitudinal axis when moving the at least one magnetic field generating element from the first position to the second position.

19. The purification method of claim 12, wherein applying the magnetic field to hold the first and second quantities of magnetic beads against the interior surface of the second container comprises positioning a first permanent magnet and a second permanent magnet on opposite sides of the container.

20. The purification method of claim 12, wherein applying the magnetic field to hold the first and second quantities of magnetic beads against the interior surface of the second container comprises arranging a plurality of permanent magnets around a perimeter of the second container at equally spaced intervals, and optionally wherein each permanent magnet of the plurality of permanent magnets has a maximum magnetic pull force equal to or greater than 100 N.

* * * * *